United States Patent [19]

Sakamoto et al.

[11] Patent Number: 4,755,293
[45] Date of Patent: Jul. 5, 1988

[54] HIGH DENSITY FILLER TYPE FILTRATION EQUIPMENT

[75] Inventors: Kiyoaki Sakamoto, Hofu; Yasuhiro Nakahara, Yamaguchi, both of Japan

[73] Assignee: Toyo Soda Manufacturing Co., Ltd., Shinnanyo, Japan

[21] Appl. No.: 77,893

[22] Filed: Jul. 27, 1987

[30] Foreign Application Priority Data

Jul. 25, 1986 [JP] Japan .................................. 61-175263

[51] Int. Cl.4 ................................................ B01D 15/08
[52] U.S. Cl. ............................ 210/198.2; 210/232; 210/450
[58] Field of Search ............... 210/198.2, 232, 282, 210/450; 55/386

[56] References Cited

U.S. PATENT DOCUMENTS 3,474,908 10/1969 Catravas ......................... 210/198.2
4,280,905 7/1981 Gunkel ............................ 210/198.2
4,283,280 8/1981 Brownlee ........................ 210/198.2
4,554,071 11/1985 Ruijten ........................... 210/198.2
4,557,830 12/1985 Onitsuka ......................... 210/198.2
4,627,918 12/1986 Saxena ............................ 210/198.2

Primary Examiner—Ernest G. Therkorn
Attorney, Agent, or Firm—Oblon, Fisher, Spivak, McClelland & Maier

[57] ABSTRACT

An elongate cylindrical column body has a flange at an open end and an annular extension extending beyond the flange in a direction of the length of the column body. The cover has a seal ring fitted therein for supporting a partition member. The seal ring is sized and shaped so that when the cover is placed on the open end of the column body, the seal ring and a guide face defined by the annular extension sealingly overlap one another by a predetermined length. Bolts passing through the flanges of the column body and cover are used to lock the cover onto the column body.

7 Claims, 6 Drawing Sheets

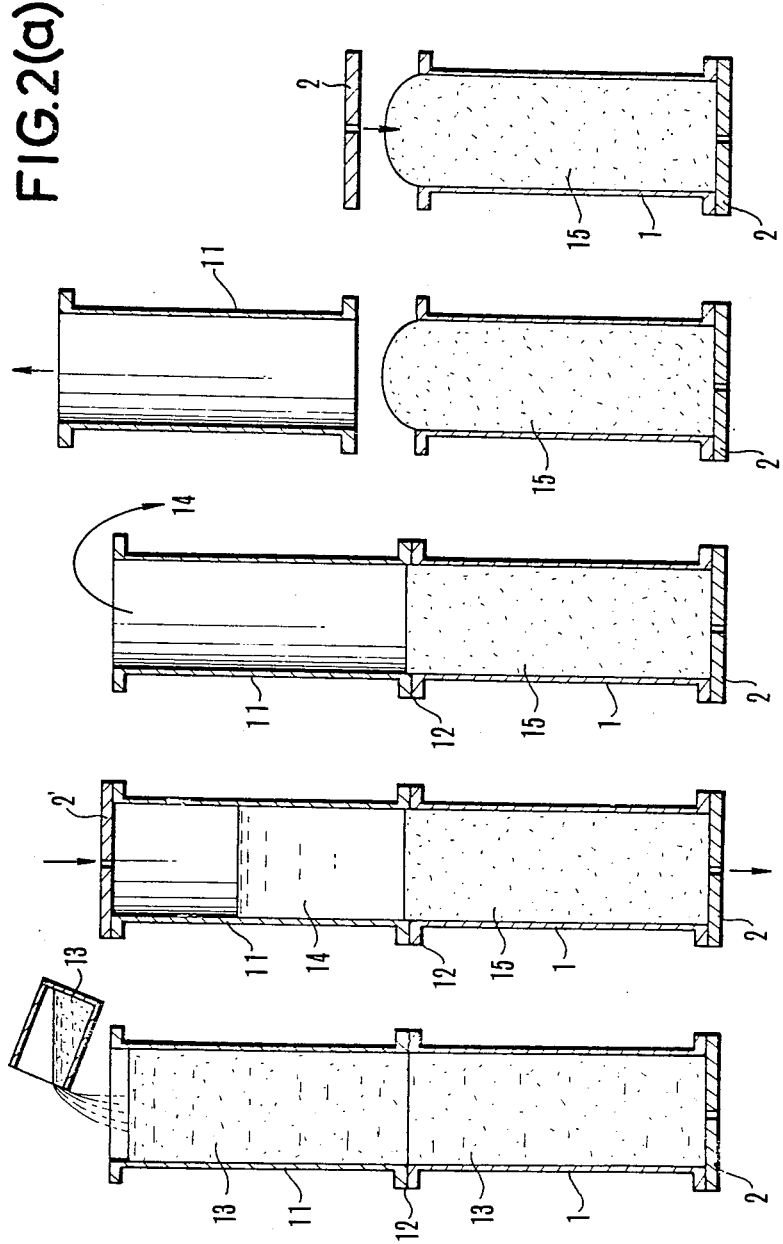

HIGH DENSITY FILLER TYPE FILTRATION EQUIPMENT

BACKGROUND OF THE INVENTION

1. Field of the Invention

This invention relates generally to filtration equipment capable of high density filling of the fillers for liquid chromatography, and more particularly high density filler type filtration equipment for analyzing specific materials in the liquid, or the separating and recovering thereof.

2. Description of the Related Art

A column for liquid chromatography as generally known in filtration equipment has a comparatively small scale of quantity. The equipment will be described by referring to a conventional liquid chromatograph. The equipment is used for separating or isolating specific materials in the liquid by the difference of permeating speeds when the liquid is passed through the fluid paths installed on the cover of a cylindrical casing, wherein fillers are filled in the column and both ends of the column are sealed.

As for the fillers used for the column, it is common to use inorganic powders (such as silica), resin powders (such as polystyrene resin, acrylate resin) usually in fine grains with diameters of under several hundred $\mu$m, or organic resin powders (such as polystyrene resin, acrylate resin) in slurry conditions to fill in the column.

Furthermore, it is functionally necessary for the column to pass the process liquid but to prevent the fillers within the column from flowing out. Water permeable filter cloths or multi-hole filter plates are installed inside of both ends of the cover of the column as partition membranes. Generally, synthetic resin membranes and filter cloths are used as partition membranes when applying low pressure for the liquid to pass, and solid partition membranes of the multi-hole plate type, such as stainless steel sintered plates, are used when applying high pressure.

Recently, demand has been increasing for the refinement and recovery of the prescribed materials by using the aforementioned column on an industrial scale. In this case, merely expanding the scale of equipment used in the testing room or laboratory will cause various problems to arise from the points of view of workability, especially in safety, and operation for assembling the equipment or replacing parts.

For example, large sized equipment requires large diameter covers to be inserted on open ends of the cylindrical casing of the column. Accordingly, the weight of the covers increases and in some cases it amounts to several tens of kilograms to several hundreds of kilograms. Therefore, machines such as hoists are required to set the cover. In that case, simplification of the work of using such a machine for setting is strongly needed and the structure of the column should be designed in conformity with this need.

For example, FIG. 5(a) and FIG. 5(b) show examples of a structure of the equipment used in the test room and the laboratory. Concerning the cover 22 which is attached to the column body 21, FIG. 5(a) is an example of the structure to which a cloth partition membrane 25 is pre-installed and FIG. 5(b) is an example of the structure to which a solid partition membrane formed of the multi-hole plate 27 is pre-installed.

In FIG. 5(a), when a filter cloth 25 or the like is installed to the cover 22, a shaping ring 25a as an auxiliary elastic member for press-fitting is suitably fixed in the inner circumferential groove of the cover 22. Even in that case, high tension of the filter cloth is required to keep the cloth from falling due to dead weight. Thus, shortcomings such as deformations of the shape and size of the filter cloth apertures are observed.

In FIG. 5(b), on the other hand, a seal ring 26 such as PTFE (polytetrafluoroethylene and the like) is used for installing the multi-hole plate 27 as a solid partition membrane in the cover 22. The coefficient of friction is small in PTFE and so extremely high precision in dimensional accuracy is required for the solid partition membrane 27 of the multi-hole plate having a large diameter of more than 200 mm to be frictionally gripped. Besides, temperature change is taken into consideration for elasticity and so the exact installation is difficult. Moreover, when ease of replacing the parts is taken into consideration, such structures as mentioned above are impractical for use. Furthermore, various methods such as calking, fitting with screws or fitting with pins may be applied for fixing the aforementioned partition membrane to the cover. But these methods may make it impossible to replace the partition plate upon the occurrence of partial standing fluids and corrosion. Accordingly, these methods are not suitable for a fluid process type column.

From the viewpoints mentioned above, the present inventors developed filtration equipment in which the partition membrane and the seal ring are installed in the cover beforehand for the purpose of simplicity when the equipment is assembled. FIG. 6 shows a column provided with such a structure. The equipment shown in FIG. 6 is not admitted to be prior art and has the following structure: An outer circumferential flange 1a of column body 1 is used for detachably connecting a cover 2 around the upper end of the column body. The cylindrical column body 1 is filled with filler. The cover 2 has a fluid path 2a and is lockably attached to the upper open end of the column body 1 to seal the upper open end when the aforementioned fillers are filled. A seal ring 6 is prearranged on a flange which extends downward from the circumference of the cover 2, is inserted in a groove on the outer circumferential flange of the column body 1 and seals the flange when lockable attachment is made by bolts 3 passing through holes 1b and 2b. The structure of the plate 7 and ring 6 is preattached to the cover and prevents the filler within the column body from flowing out when the cover is press-fitted on the column body.

The objective of improving the assembling of a column for liquid chromatography is attainable by the structure mentioned above, however since the column is used for separating the prescribed materials, a predetermined separation capability ought to be maintained. High density filling of the filler is required for the purpose.

When the filler is filled into the column for liquid chromatography, a common technique is that filler powders are mixed with liquid to make slurry, which is poured into the column, and the liquid is extracted to attain high density, uniform filling of the filler within the column. Such a filling operation cannot be easily realized even with the improved filtration equipment of FIG. 6. This is due to the fact that the slurry overflows from the upper end of the column body when the cover is attached to the column body.

SUMMARY OF THE INVENTION

The object of this invention is to provide high density filler type filtration equipment which can successfully realize extremely high density and uniform filling of the column fillers and in which it is easy to assemble and replace the parts when the separation, refinement and recovery of the prescribed materials are performed on an industrial scale.

The high density filler type filtration equipment of the invention comprises an elongate cylindrical column body having at least an upper open end, flange means adjacent the open end and an annular extension extending beyond the flange means in the direction of the length of the column body. A cover having a fluid path has mounted thereto a partition member and seal ring. The seal ring comprises means for sealing the open end when the cover is placed on the open end, wherein the annular extension and the seal ring overlap one another by a predetermined length when the cover is placed on the open end and wherein the annular extension and the seal ring are sized such that the annular extension defines a guide face along which the seal ring sealingly slides as the cover is placed on the open end. Means are provided for locking the cover on the open end.

This invention can be favorably applied to a column with a diameter of more than 50 mm generally, but more favorably more than 100 mm and further more than 200 mm. But this does not mean that this invention is not applicable to the columns with a diameter less than that described above.

The column which is composed according to this invention can be applied to various compositions and objects according to the kinds of fillers and process water used, and the materials to be taken out.

For example, as fillers for liquid chromatography, activated carbon, silica gel, ion exchange resin and the like may be mentioned as the fillers to be used.

Moreover, applicable fields for the column of this invention are, for example, refinement and recovery of materials such as proteins, enzymes, vitamins and sugar, refinement and recovery of drugs (for example, insulin and the like) and effluent disposal and the like.

Filling the fillers can be performed in a known way. As a main body of the equipment of this invention, the column body may be made of metal, synthetic resin (acrylic, vinyl chloride, etc.) for fairly low strength requirements, inorganic compounds (glass, ceramics, etc.) or carbon steel, the inner side of the column being coated with PTFE etc. One end open type, or both ends open type, columns may be used. A cylindrical column of stainless steel is adopted generally in consideration of corrosion resistance, chemical resistance, machining, and strength of the structure and the like. A cover which is used to seal the open end of the column body is made preferably of the same material that is used for the column body. On the cover, the fluid path through which the process fluid passes is usually piercedly formed at one point in the neighborhood of the center, or in a plurality of points at the center or its surroundings. A seal ring of PEFE, polyethylene, hard rubber, and the like is beforehand attached to the cover. The seal ring is inserted in the inner circumferential groove by the elasticity of the ring itself. The seal ring is used for ensuring sealing by press-fitting with the column body. At the same time, the ring may serve as a stopper ring to prevent the falling down of the partition membrane. This may be effective for decreasing the number of parts and simplifying the assembly work.

Examples of the partition membrane which is used in this invention for low pressure operations are soft membranes such as cloth or sheets which pass the fluid. But in this case, supporting members such as a net or plate should be inserted between the soft membrane and the recessed bottom of the cover. Rectification of the flow of the process fluid may be given to the supporting members by means such as a net and the like.

A multi-hole sintered body of the metal powder and the like having enough mechanical strength by itself can be used for partition membranes in high pressure operations. Generally, stainless sintered plates are used.

In the equipment of this invention, when the cover is attached to the column body, the extension defining the guide face of the column body, which is formed to slide in a liquid sealed condition with the seal ring, is provided to have a prescribed length in the direction of the length of the column body. The length of the extension may be designed to be an adequate length according to the kind of filler used, degree of filling and the conditions of the filling (conditions of slurry), but generally in most cases it is approximately several mm to 30 mm, preferably 5 mm to 20 mm. When the length is below several milimeters, practical merits for high density uniform filling cannot be obtained under this invention.

Furthermore, this invention is provided as a suitable structure for filling the filler into the column in high density but this does not mean the column of the structure in this invention cannot be used for low density filling and the like. The column for fluid chromatography to which this invention is applied may be used for either analyzing or separating due to the objective classification. It may be used also for gel filtration chromatography or ion exchange chromatography or affinity chromatography or water chromatography.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2(a) shows an assembly procedure for the column body device of the invention;

DETAILED DESCRIPTION OF THE PREFERRED EMBODIMENTS

Figure 1:
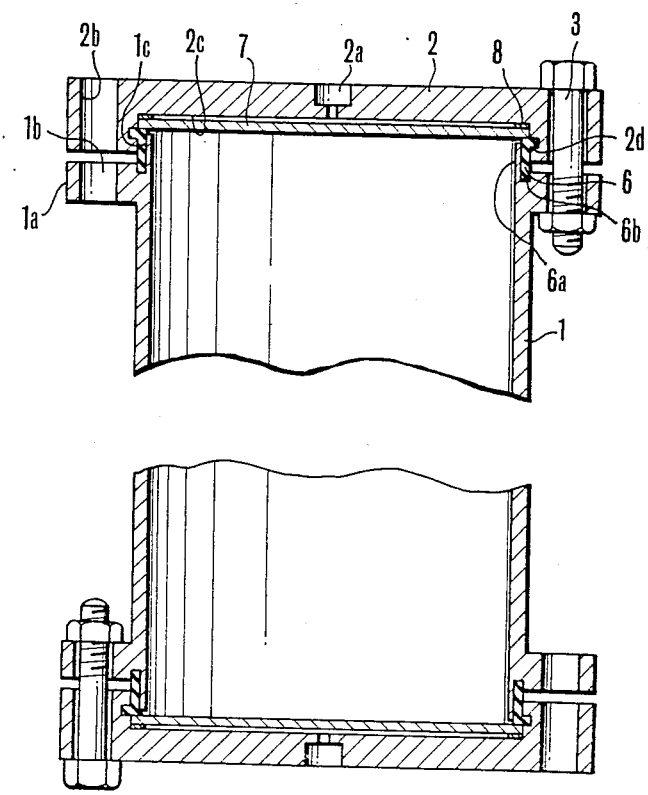
FIG. 1 is a longitudinal sectional view showing an embodiment of a high density, uniform filler type filtration equipment according to this invention.

The preferred embodiments of this invention will be described referring to the drawings.

In FIG. 1, a column body 1 has a shape which is formed into a cylinder with both its ends opened. Near the upper and lower ends are formed annular end flanges 1a protruded on the outer circumference of the cylinder. Bolt holes 1b are formed on the end flanges 1a.

At the inner periphery of each of the end flanges 1a is formed a circumferential groove 6b in which the end of a seal ring 6, which will be described later, is to be lockably inserted. An annular extension 1c of the column body extending beyond the flange 1a in the direction of the length of the column body defines a guide face at the outer circumferential side face of the column body and has a predetermined length at both ends of the column body. A cover 2 is lockably fitted to each end of the column body. On the circumferential edge of the cover is formed a bolt hole 2b which is opposed to the bolt hole 1b of the end flange 1a. A fluid path 2a is provided for the process liquid to flow when the equipment is in use after assembly. An inner recess 2c is formed in the cover, in the inner circumference of which are installed the seal ring 6 (FIG. 3), stainless steel multi-hole plate 7 as a partition membrane, and a ring gasket 8 prior to assembly of the equipment.

A circumferential groove 2d formed on the circumferential wall of the inner recess 2c acts as the fixture of the seal ring 6 which forms a stopper for mounting the stainless multi-hole plate 7. Tightening bolts 3 and nuts are used for tightly fixing the column body 1 and the cover 2 with the seal ring 6 in between, to assemble the equipment.

The filtration equipment of this embodiment can be assembled in the condition where the guide face formed by the extension 1c at the end of the column body 1 and the seal ring 6 which is sealingly and elastically fitted around the extension 1c are slidably and sealingly overlapped by a definite length. Assembly is performed, as shown in FIG. 2(a) and FIG. 2(b), such that the filler slurry which is filled up to the upper end of the column body 1 in a convex shape is prevented from flowing out when assembly is finished, so that high density and uniform filling of the filler within the column body 1 is attained.

Figure 2B:
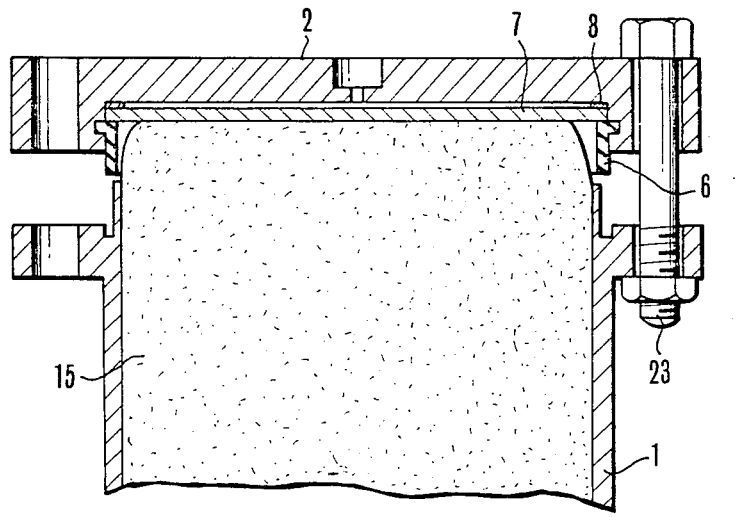
FIG. 2(b) shows the conditions before and after the cover is attached to the device.
Figure 2B:
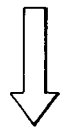
Figure 2B:
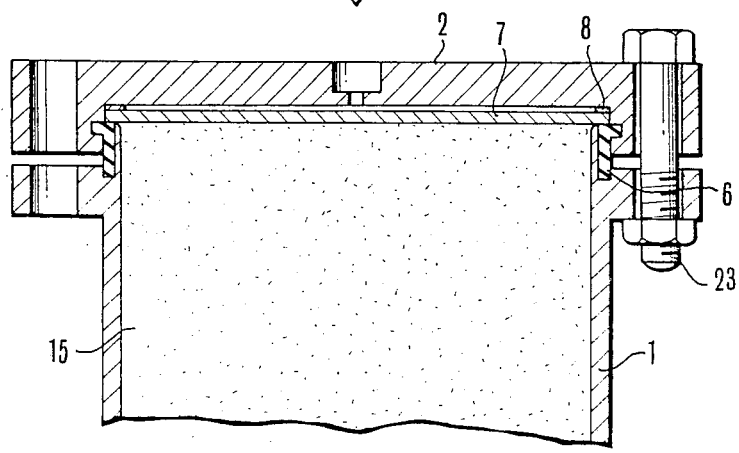

FIG. 2(a) is a view showing the assembly procedure of the equipment in FIG. 1, which procedure is similar to the known one. A reservoir 11 (a further column body may be used) is connected to the upper end of the column body 1, by setting the bottom end of the reservoir on the cover 2 with a gasket 12 for preventing liquid leaks therebetween. Slurry 13 containing a predetermined quantity of the filler is poured into the upper end of the reservoir 11. After that, a cover 2' is put on the upper end of the reservoir 11 and the slurry is forced into the column body 1 by applying pressure with a high pressure pump which is not shown. After applying pressure, the cover 2' on the upper end is removed and liquid 14 in the reservoir 11 is pumped out. After pumping out, the reservoir 11 is removed. A filler 15 which has remained at the bottom of the reservoir 11 then remains heaped up in the column body 1 (top of FIG. 2(b)). A cover 2, to which is beforehand installed functional parts such as the stainless multi-hole plate as is shown in FIG. 1, is then set and tightened with fastening bolts 23 and nuts as shown in an enlarged view of FIG. 2(b). The filling of the filler 15 into the column body 1 is then finished.

Figure 3:
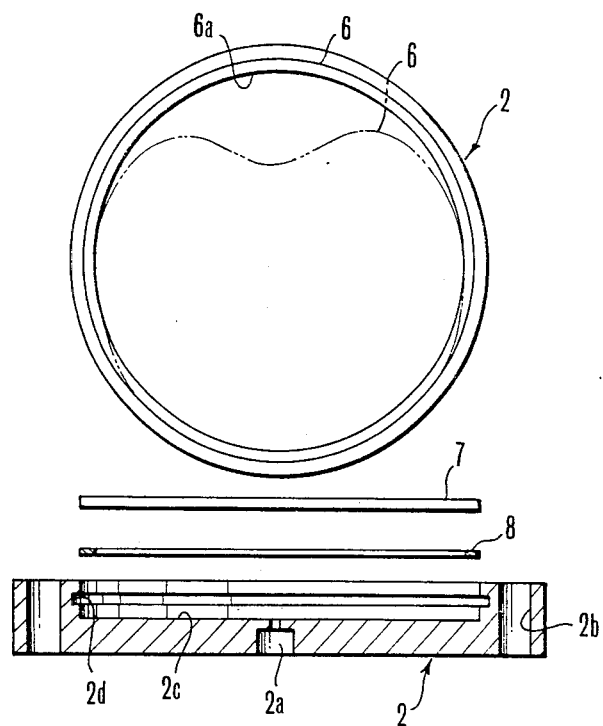
FIG. 3 is a development view of the parts of the cover.
Figure 6:
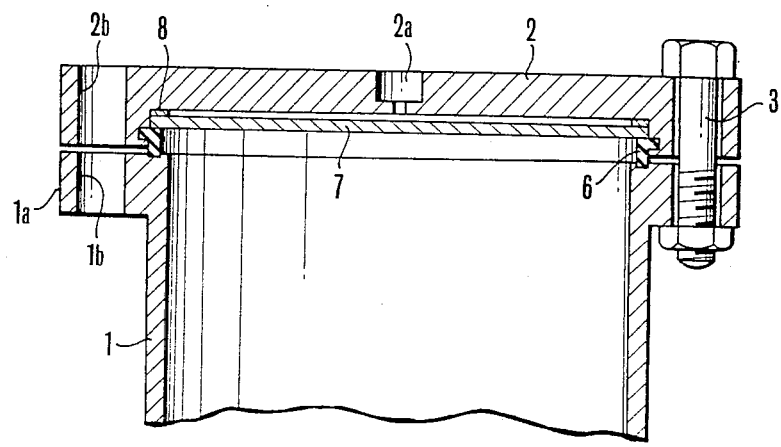
FIG. 6 is a longitudinal sectional view of filtration equipment for explaining a comparative example of this invention.

FIG. 3 is a view illustrating the preparatory assembly work of the cover 2 which is prepared in a condition such that the seal ring 6 and the like is attached when the aforementioned assembly is accomplished. The ring gasket 8 is first put on the bottom of an inside recess 2c of the cover 2, on which the stainless multi-hole plate 7 is put. Then, the seal ring 6 is fixed in the inner circumferential groove 2d. Preparatory assembly of the cover applicable to the equipment which is shown in FIG. 2(a) and FIG. 2(b) is thus established. It has been confirmed that the filtration equipment which is prepared in such a way has a high degree of filling when compared with the filling condition of the filler which is obtained in the filtration equipment the structure of which is shown in FIG. 6.

The following Table 1 shows the results of a Theoretical Plate showing the column capability and maximum allowable flow velocity when the same filler materials are filled and the predetermined processing liquids are filtered in the following equipment: The filtration equipment with columns A, B, C according to the invention, each of which has an extension 1c with a length of 7 mm in the direction of the length of the column body of FIG. 1, and the filtration equipment D, E, F shown in FIG. 6 as a comparative example, which has the same dimensions as the three columns (A, B, C) of the invention except that they lack the extension defining the guide face.

The inner diameter of the column used was 301.5 mm, effective length 600 mm, pressure resistance 5 kg/cm$^2$, material SUS 316 (materials of the reservoir are the same as that of the column). The filler used was TSK-GEL TOYOPEAL HW-55F (Toyo Soda Manufacturing Co., Ltd.). Filling requirements were as follows: pure water was used as the filling solvent, slurry density was 60 vol %, pressure 1.5/cm$^2$G, final velocity at filling pressure was 18-20 ml/cm$^2$.hr.

An amount of 150 ml of cattle serum-albumin was used as comparative verification materials for both the embodiment of the invention and comparative examples. Processing liquid was phosphate buffer pH 6.8 (potassium dihydrogenphosphate, sodium dihydrogenphosphate = 1 : 1). Processing speed was 10 ml/cm$^2$.hr. Theoretical Plate and flow velocity was gradually increased from obtained chromatogram to determine maximum allowable flow velocity. From the result of Table 1, Theoretical Plate and maximum allowable flow velocity of equipment according to the invention is extremely high when compared with that of the comparative examples. Therefore, it is clear that high density and uniform filler is filled in the filtration equipment.

Figure 4:
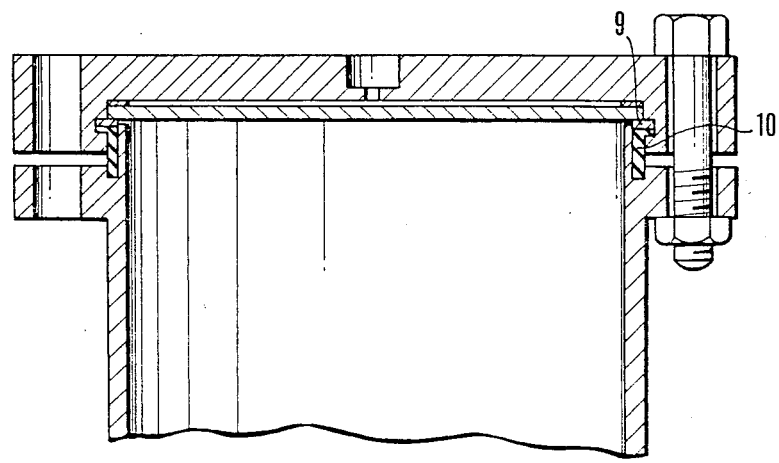
FIG. 4 is a longitudinal sectional view of the filtration equipment showing another embodiment of the invention.
Figure 5A:
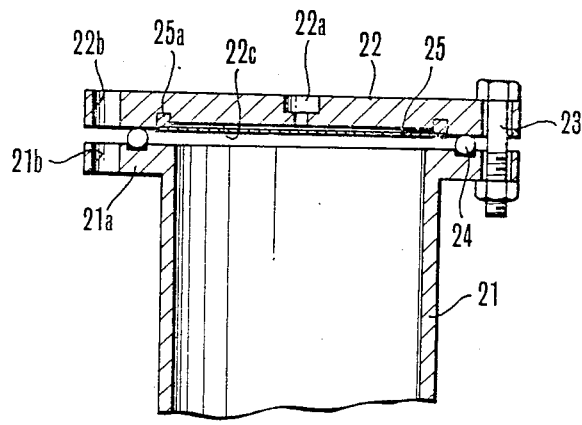
FIG. 5(a) and FIG. 5(b) are views showing the attached conditions of the conventional type cover.
Figure 5B:
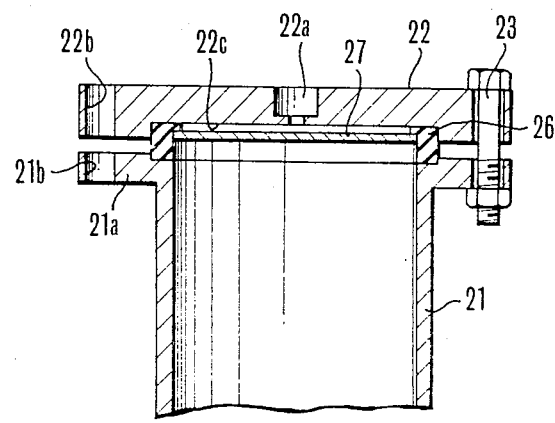

FIG. 4 is a view showing another embodiment of the invention, wherein a stopper member 9 for preventing the partition membrane from coming out of the cover and a seal ring 10 are constituted as separate bodies. The rest is the same structure as in the first embodiment.

Similar effect can be obtained from this embodiment as from the aforementioned embodiment.

According to the high density, uniform filler type filtration equipment as described above, high density and uniform filling of the filler is possible, so that sophisticated equipment to perform the refining and collecting of the objective material in the liquid on an industrial scale is realized. Assembly and parts replacement are also made easy and the implementation on an industrial scale can be favorably performed.

Furthermore, according to the equipment of this invention, high density and uniform filling of the filer can be realized with the aforementioned structure which is easy to operate. Therefore, it is applicable to equipment for refinement and collection of various valuable materials, and its utility is extremely high.

Obviously, numerous modifications and variations of the present invention are possible in light of the above teachings. It is therefore to be understood that within the scope of the appended claims, the invention may be practiced otherwise than as specifically described herein.

TABLE 1

|  | Theoretical Plate (TP/60 cm) | Maximum Allowable Flow Velocity (ml/cm$^2$ · hr) |
|---|---|---|
| Invention: | | |
| A | 1900 | 12 |
| B | 2200 | 13 |
| C | 2100 | 12 |
| Comparative Example: | | |
| D | 1500 | 9 |
| E | 1400 | 9 |
| F | 1400 | 10 |

What is claimed as new and desired to be secured by Letters Patent of the United States is:

1. High density filler type filtration equipment for liquid chromatography comprising:
   an elongate cylindrical chromatography column body having at least an upper open end, flange means adjacent said open end and an annular extension extending beyond said flange means in a direction of the length of said column body;
   a cover having a fluid path;
   a partition membrane;
   means for mounting said partition membrane to said cover;
   a seal ring mounted to said cover and comprising means for sealing said open end of said column body when said cover is placed on said open end, wherein said annular extension and said seal ring overlap one another by a predetermined length when said cover is placed on said open end and wherein said annular extension and said seal ring are sized such that said annular extension defines a guide face along which said seal ring sealingly slides as said cover is placed on said open end, and means for locking said cover on said open end.

2. The equipment of claim 1, wherein said seal ring comprises said means for mounting said partition membrane.

3. The equipment of claim 2, wherein said cover includes an annular flange having an inner periphery with a circumferential groove and wherein said seal ring is fitted in said circumferential groove.

4. The equipment of claim 3, including a further circumferential groove in said column body and surrounding said exterior, wherein said seal ring fits in said further circumferential groove when said cover is placed on said open end with said extension and seal ring overlapping one another.

5. The equipment of claim 1, wherein said cover includes an annular flange having an inner periphery with a circumferential groove, further including a stopper member separate from said seal ring fitted in said groove, said stopper member comprising said means for mounting said partition membrane.

6. The equipment of claim 1, wherein said partition membrane comprises a multi-hole stainless steel sintered plate.

7. The equipment of claim 1, wherein said extension has a length of between 5 mm and 20 mm.

* * * * *